US00PP12602P2

(12) United States Plant Patent
Sorensen

(10) Patent No.: US PP12,602 P2
(45) Date of Patent: May 7, 2002

(54) OSTEOSPERMUM PLANT NAMED 'AKNAM'

(75) Inventor: Carl Aksel Kragh Sorensen, Aabyhoj (DK)

(73) Assignee: Paul Ecke Ranch, Encinitas, CA (US)

( * ) Notice: Subject to any disclaimer, the term of this patent is extended or adjusted under 35 U.S.C. 154(b) by 101 days.

(21) Appl. No.: 09/722,182

(22) Filed: Nov. 27, 2000

(51) Int. Cl.[7] ..... A01H 5/00
(52) U.S. Cl. ..... Plt./360

(58) Field of Search ..... Plt./360

*Primary Examiner*—Amy J. Nelson
*Assistant Examiner*—Susan B. McCormick
(74) *Attorney, Agent, or Firm*—C. A. Whealy

(57) ABSTRACT

A distinct cultivar of Osteospermum plant named 'Aknam', characterized by its uniformly mounded, outwardly spreading and compact plant habit; very freely branching growth habit; full and dense plants; freely flowering with numerous inflorescences per plant; spoon-shaped ray florets; and white-colored ray and disc florets.

1 Drawing Sheet

BACKGROUND OF THE INVENTION

The present Invention relates to a new and distinct cultivar of Osteospermum plant, botanically known as *Osteospermum ecklonis*, and hereinafter referred to by the cultivar name Aknam.

The new Osteospermum is a product of a planned breeding program conducted by the Inventor in Aabyhoj, Denmark. The objective of the breeding program is to create new Osteospermum cultivars with interesting ray floret colors and spoon-shaped ray florets.

The new Osteospermum originated from a cross made by the Inventor of an unidentified proprietary *Osteospermum ecklonis* seedling selection as the male, or pollen, parent with the proprietary *Osteospermum ecklonis* selection identified as code number 97008 as the female, or seed, parent. The new Osteospermum was discovered and selected by the Inventor as a single flowering plant within the progeny of the stated cross grown in a controlled environment in Aabyhoj, Denmark, in 1998.

Asexual reproduction of the new Osteospermum by vegetative tip cuttings was first conducted in Aabyhoj, Denmark in 1998. Asexual reproduction by cuttings has shown that the unique features of this new Osteospermum are stable and reproduced true to type in successive generations.

SUMMARY OF THE INVENTION

The cultivar Aknam has not been observed under all possible environmental conditions. The phenotype may vary somewhat with variations in environment such as temperature, daylength, light intensity, water status, and fertility levels without, however, any variance in genotype.

The following traits have been repeatedly observed and are determined to be the unique characteristics of 'Aknam'. These characteristics in combination distinguish 'Aknam' as a new and distinct Osteospermum:

1. Uniformly mounded, outwardly spreading and compact plant habit.

2. Very freely branching growth habit; full and dense plants.

3. Freely flowering with numerous inflorescences per plant.

4. Spoon-shaped ray florets.

5. White-colored ray and disc florets.

Compared to plants of the parent selections, plants of the new Osteospermum are more compact and differ in ray floret coloration.

The new Osteospermum can be compared to the *Osteospermum ecklonis* culltivar Aksillo, disclosed in U.S. Plant Pat. application Ser. No. 09/422,169. In side-by-side comparisons conducted in Encinitas, Calif., plants of the new Osteospermum differ from plants of the cultivar Aksillo in the following characteristics:

1. Plants of the new Osteospermum have slightly larger inflorescences, more ray florets, larger discs and more disc florets than plants of the culitvar Aksillo.

2. The upper surface of the ray florets of plants of the new Osteospermum is not as pure white in color as the upper surface of ray florets of plants of the cultivar Aksillo.

3. The lower surface of the ray florets of plants of the new Osteospermum is white and pale yellow in color whereas the lower surface of ray florets of plants of the cultivar Aksillo is blue purple.

4. Disc florets of plants of the new Osteospermum are white in color whereas disc florets of plants of the cultivar Aksillo are blue purple.

BRIEF DESCRIPTION OF THE PHOTOGRAPHS

The accompanying colored photographs illustrate the overall appearance of the new Osteospermum showing the colors as true as it is reasonably possible to obtain in colored reproductions of this type. Colores in the photographs may differ from the color values cited in the detailed botanical description which accurately describe the colors of the new Osteospermum.

The photograph at the top of the sheet comprises a side perspective view of a typical flowering plant of 'Aknam'.

The photograph at the bottom of the sheet is a close-up view of typical leaves, inflorescences and flower buds of 'Aknam'.

DETAILED BOTANICAL DESCRIPTION

In the following description, color references are made to The Royal Horticultural Society Colour Chart except where general terms of ordinary dictionary significance are used. The following observations and measurements describe plants grown and flowered during the spring in Encinitas, Calif., under outdoor conditions which approximate those generally used in commercial production. One rooted cutting was planted in a 20-cm container and pinched once. Measurements and numerical values represent averages of typical flowering plants about 22 weeks after planting.

Botanical classification: *Osteospermum ecklonis* cultivar Aknam.

Parentage:

*Male, or pollen, parent.*—Unidentified proprietary Osteospermum ecklonis seedling selection, not patented.

*Female, or seed, parent.*—Proprietary *Osteospermum ecklonis* seedling selection code number 97008, not patented.

Propagation:

*Type.*—Terminal cuttings.

*Time to initiate rooting.*—About 8 days at 18° C.

*Time to develop roots.*—About 23 days at 18° C.

*Root description.*—Fibrous and well-branched.

Plant description:

*Appearance.*—Perennial herbaceous container and garden plant. Uniformly mounded and compact plant habit; upright to outwardly spreading. Very freely branching, about 16 lateral branches develop after pinching; dense and full plants. Moderately vigorous growth habit.

*Plant height.*—About 24 cm.

*Plant width or area of spread.*—About 50 cm.

*Lateral branches.*—Length: About 12 cm. Diameter: About 8 mm. Internode length: About 1 cm. Strength: Strong. Texture: Glabrous. Color: 144A.

*Foliage description.*—Arrangement: Leaves single and alternate. Number of leaves per lateral branch: About 13. Length: About 4 cm. Width: About 2 cm. Shape: Elliptic. Apex: Broadly acute. Base: Attenuate. Margin: Irregular serrations. Texture: Coarse, leathery, glandular and glabrous. Color: Young foliage upper surface: 146A. Young foliage lower surface: 146B. Mature foliage upper surface: 146A. Mature foliage lower surface: 146A. Venation, both surfaces: 146B. Petiole length: About 1.2 cm. Petiole diameter: About 4 mm. Petiole color: 146C.

Inflorescence description:

*Appearance.*—Terminal and axillary inflorescences held above and beyond the foliage on moderately strong axillary peduncles. Composite inflorescence form with sproon-shaped ray florets and disc florets massed at the center; ray and disc florets arranged acropetally on a capitulum. Not fragrant. Inflorescences persistent.

*Flowering response.*—Plants flower continuous and freely from the spring through the fall.

*Postproduction longevity.*—Inflorescences maintain good color and substance for about 4 to 7 days in an outdoor environment dependent on temperature and weather conditions.

*Quantity of inflorescences.*—About 100 open inflorescences and buds per plant.

*Inflorescence bud* (*at stage of showing color*).—Length: About 1.5 cm. Diameter: About 9 mm. Shape: Ovoid. Color: Close to 150B.

*Inflorescence size.*—Diameter: About 5.25 cm. Depth (height): About 1.3 cm. Diameter of disc: About 1.3 cm.

*Ray florets.*—Length: About 2.7 cm. Width: Apex and base, about 6 mm; at indentation, about 2 mm. Shape: Spoon. Apex: Rounded to emarginate. Base: Acute. Margin: Entire. Texture: Satiny. Orientation: Initially upright, outer florets perpendicular to peduncle then reflexing. Number of ray florets per inflorescence: About 26 in a single whorl. Color: When opening, upper surface: 155B. When opening, lower surface: 155A. Fully opened, upper surface: 155C to 155D. Fully opened, lower surface: 155B at apex and base; mid-section, 1C.

*Disc florets.*—Shape: Tubular, elongated. Apex: Five-pointed. Length: About 8 mm. Width: About 3 mm. Number of disc florets per inflorescence: About 140. Color: Immature: 155A. Mature: 155C.

*Phyllaries.*—Length: About 8 mm. Whorl diameter: About 2.3 cm. Shape: Linear. Apex: Acute. Margin: Entire. Texture: Somewhat rough with tiny hairs. Number per inflorescence: About 18 in a single whorl. Color: Upper surface: 138B. Lower surface: 138A.

*Peduncles.*—Length, terminal peduncle: About 9.5 cm. Length, second peduncle: About 10.5 cm. Length, third peduncle: About 11.5 cm. Angle: Terminal peduncles, erect; secondary peduncles, about 45° from vertical. Strength: Moderate. Texture: Coarse with tiny scattered short hairs. Color: 144A.

*Reproductive organs.*—Androecium: Present on disc florets only. Stamen number: Five, fused. Anther shape: Oblong. Anther size: About 3 mm by 1 mm. Anther color: 163A. Pollen amount: Scarce. Pollen color: 23A. Gynoecium: Present on both ray and disc florets. Pistil number: One. Pistil length: About 6 mm. Stigma shape: Bipartite. Stigma color: 155A. Style length: About 4 mm. Style color: 155B. Ovary color: 1B.

*Seed.*—Seed production has not been observed.

Disease resistance: Resistance to pathogens common to Osteospermums has not been observed on plants grown under commercial greenhouse or outdoor conditions.

It is claimed:

1. A new and distinct cultivar of Osteospermum plant named 'Aknam', as illustrated and described.

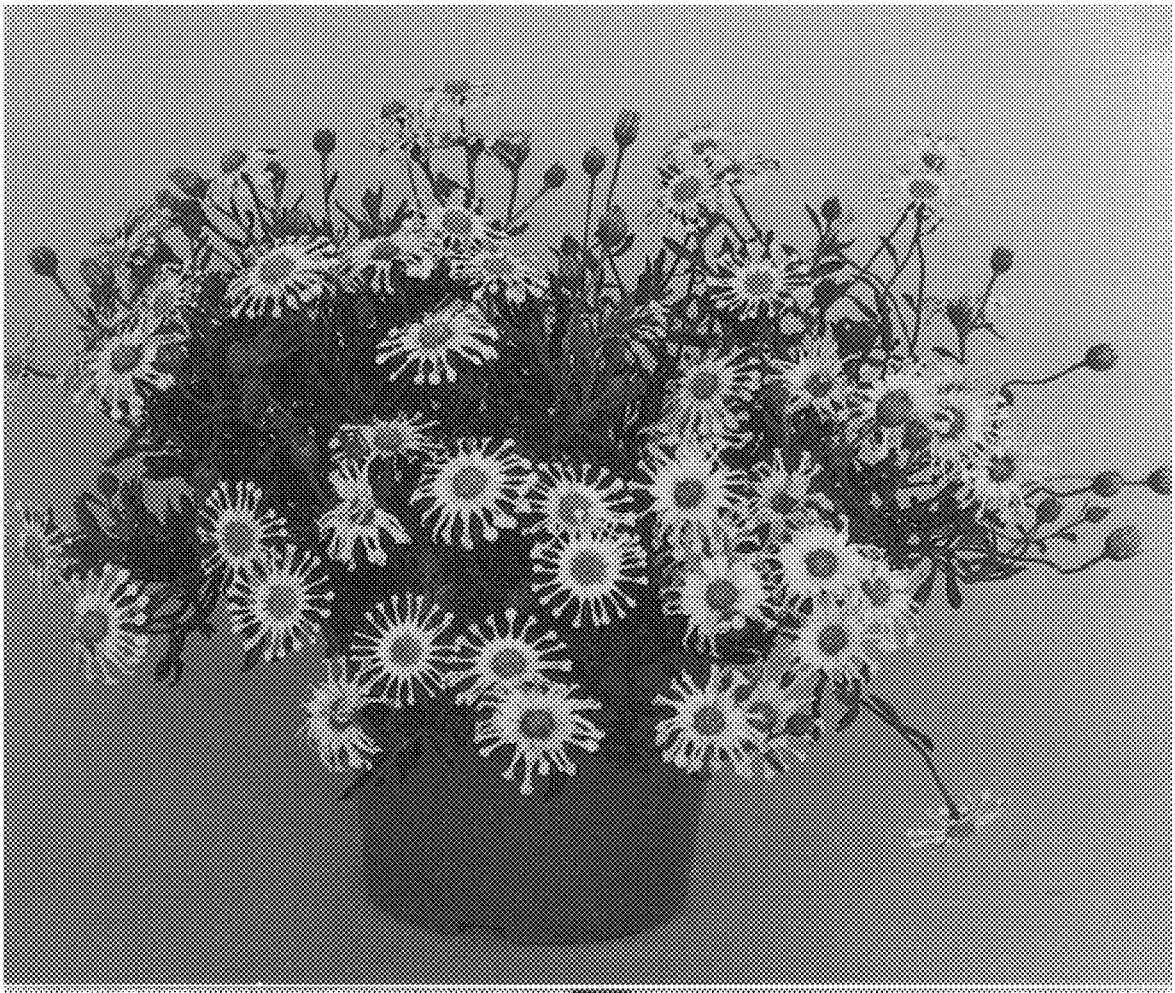
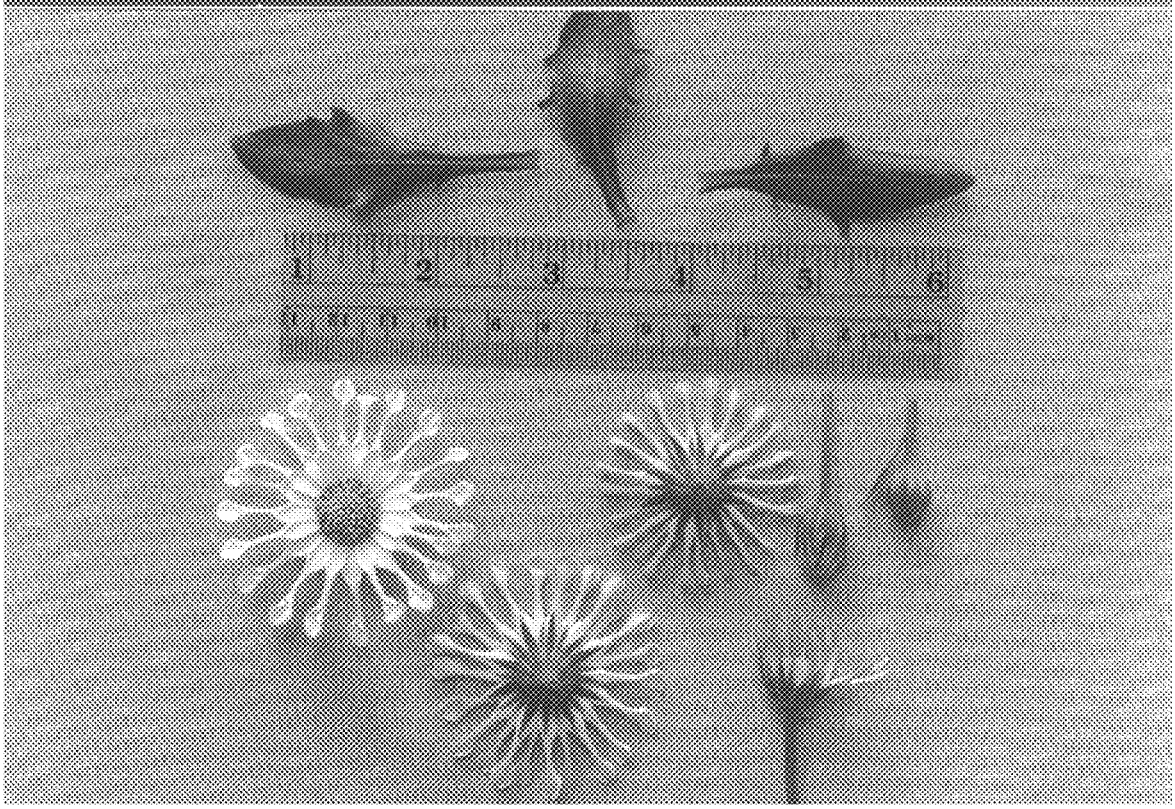

* * * * *